US00PP19709P2

(12) United States Plant Patent
Jaldety et al.

(10) Patent No.: US PP19,709 P2
(45) Date of Patent: Feb. 10, 2009

(54) ***ANGELONIA* PLANT NAMED 'ZEBRA'**

(50) Latin Name: *Angelonia augustifolia*
Varietal Denomination: Zebra

(76) Inventors: Erella Jaldety, 9 Alon Street, Kfar Hanagid (IL), 76875; Nathan Jaldety, 9 Alon Street, Hfar Hangid (IL), 76875

( * ) Notice: Subject to any disclaimer, the term of this patent is extended or adjusted under 35 U.S.C. 154(b) by 0 days.

(21) Appl. No.: 11/903,540

(22) Filed: Sep. 21, 2007

(51) Int. Cl.
*A01H 5/00* (2006.01)

(52) U.S. Cl. ..... Plt./404
(58) Field of Classification Search ..... Plt./404
See application file for complete search history.

*Primary Examiner*—Annette H Para
*Assistant Examiner*—Louanne C Krawczewicz Myers
(74) *Attorney, Agent, or Firm*—. C. A. Whealy

(57) ABSTRACT

A new and distinct cultivar of *Angelonia* plant named 'Zebra', characterized by its upright plant habit; freely branching habit; freely flowering habit; and red purple and purple bi-colored flowers.

1 Drawing Sheet

Botanical designation: *Angelonia augustifolia.*
Cultivar denomination: 'Zebra'.

BACKGROUND OF THE INVENTION

The present invention relates to a new and distinct cultivar of *Angelonia,* botanically known as *Angelonia augustifolia* and hereinafter referred to by the name 'Zebra'.

The new *Angelonia* is a naturally-occurring branch mutation of an unnamed selection of *Angelonia augustifolia,* not patented. The new *Angelonia* was discovered and selected by the Inventors as a single flowering plant within a population of plants of the parent selection in a controlled environment in Kfar Hanagid, Israel on May 10, 2003.

Asexual reproduction of the new *Angelonia* by cuttings in a controlled environment in Kfar Hanagid, Israel since May 10, 2003, has shown that the unique features of this new *Angelonia* are stable and reproduced true to type in successive generations.

SUMMARY OF THE INVENTION

The cultivar Zebra has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Zebra'. These characteristics in combination distinguish 'Zebra' as a new and distinct cultivar of *Angelonia:*

1. Upright plant habit.
2. Freely branching habit.
3. Freely flowering habit.
4. Red purple and purple bi-colored flowers.

Plants of the new *Angelonia* differ from plants of the parent selection primarily in flower color as plants of the parent selection have blue-colored flowers.

Plants of the new *Angelonia* can be compared to plants of the cultivar Adebic, disclosed in U.S. Plant patent application Ser. No. 11/820,016. Plants of the new *Angelonia* and the cultivar Adebic primarily in flower color as plants of the cultivar Adebic had violet and white bi-colored flowers.

BRIEF DESCRIPTION OF THE PHOTOGRAPH

The accompanying colored photograph illustrates the overall appearance of the new *Angelonia,* showing the colors as true as it is reasonably possible to obtain in colored reproductions of this type. Colors in the photograph may differ slightly from the color values cited in the detailed botanical description which accurately describe the colors of the new *Angelonia.* The photograph comprises a side perspective view of a typical flowering plant of 'Zebra' grown in a container.

DETAILED BOTANICAL DESCRIPTION

The aforementioned photograph and following observations, measurements and values describe plants grown in Kfar Hanagid, Israel during the spring in containers and under commercial practice in a polyethylene-covered greenhouse with day temperatures ranging from 24° C. to 30° C. and night temperatures ranging from 15° C. to 20° C. Plants were pinched twice, two and six weeks after planting. Plants had been growing for about six months when the photograph and description were taken. In the following description, color references are made to The Royal Horticultural Society Colour Chart, 1995 Edition, except where general terms of ordinary dictionary significance are used.

Botanical classification: *Angelonia augustifolia* cultivar Zebra.

Parentage: Naturally-occurring branch mutation of an unnamed selection of *Angelonia augustifolia,* not patented.

Propagation:

*Type.*—By cuttings.

*Time to initiate roots.*—About six to seven days at 20° C.

*Time to produce a rooted young plant.*—About 20 to 25 days at 30° C.

*Root description.*—Fibrous; yellow in color.

*Rooting habit.*—Moderate branching; moderately dense.

Plant description:

*Plant form/habit.*—Herbaceous perennial. Upright; inverted triangle. Freely branching habit; when pinched, lateral branches form at the nodes. Vigorous growth habit.

*Plant height.*—About 30 cm.

*Plant width* (*spread*).—About 25 cm.

*Lateral branches.*—Length: About 17 cm to 23 cm. Diameter: About 2 mm to 3 mm. Internode length: About 2.5 cm. Strength: Moderately strong. Texture: Smooth, glabrous. Color: 144B.

Foliage description:

*Arrangement.*—Opposite, decussate; simple; sessile.

*Length.*—About 4.5 cm to 5.5 cm.

*Width.*—About 0.9 cm to 1.2 cm.

*Shape.*—Obovate.

*Apex.*—Acute.

*Base.*—Attenuate.

*Margin.*—Towards the apex, serrate; towards the base, entire.

*Texture, upper and lower surfaces.*—Pubescent.

*Venation pattern.*—Pinnate.

*Color.*—Developing and fully expanded leaves, upper surface: 137A; venation, 139D. Developing and fully expanded leaves, lower surface: 137C; venation, 139D.

Flower description:

*Flower type/habit.*—Single flowers arranged in terminal racemes; flowers face mostly outward. Freely flowering habit; dense inflorescences with about 25 flowers per inflorescence.

*Fragrance.*—None detected.

*Natural flowering season.*—Continuously flowering from spring until autumn in Europe. Flowers not persistent.

*Postproduction longevity.*—Flowers last about two to three weeks on the plant.

*Inflorescence height.*—About 12 cm.

*Inflorescence diameter.*—About 8 cm.

*Flower buds.*—Height: About 3 mm. Diameter: About 3 mm. Shape: Globular. Color: Close to 138A.

*Flower length.*—About 2.3 cm to 3 cm.

*Flower diameter.*—About 2.4 cm to 2.8 cm.

*Flower depth.*—About 7 mm to 9 mm.

*Flower throat diameter.*—About 8 mm to 10 mm.

*Flower tube length.*—About 1 cm to 1.1 cm.

*Petals.*—Quantity per flower: Typically five in a single whorl; petals fused at the base; petals do not have glands and do not appear to have a palate. Length: About 1 cm to 1.2 cm. Width: About 1 cm to 1.1 cm. Shape: Roughly spatulate. Apex: Rounded. Margin: Entire; slightly undulate. Texture, upper and lower surfaces: Smooth, glabrous. Color: When opening and fully opened, upper surface: Close to 58B to 58C; central stripe, close to 77A. When opening and fully opened, lower surface: Close to 58B to 58C; central stripe, close to 77A. Throat: Close to 71A.

*Sepals.*—Quantity per flower: Typically five in a single whorl. Length: About 4 mm to 5 mm. Width: About 6 mm to 7 mm. Shape: Lanceolate. Apex: Acute. Margin: Entire. Texture, upper and lower surfaces: Smooth, glabrous. Color, upper and lower surfaces: 137D.

*Pedicels.*—Length: About 1.9 cm to 2.5 cm. Diameter: About 1 mm to 1.5 mm. Angle: Outwardly. Strength: Moderately strong; flexible. Texture: Pubescent. Color: Close to 146A.

*Reproductive organs.*—Stamens: Quantity per flower: Typically four. Filament length: About 4 mm to 5 mm. Filament color: Close to 155D. Anther shape: Elliptic. Anther length: About 3 mm. Anther color: Purplish. Pollen amount: None observed. Pistils: None observed.

*Seeds/fruits.*—Seed and fruit development have not been observed.

Disease/pest resistance: Plants of the new *Angelonia* have not been noted to be resistant to pathogens and pests common to *Angelonia.*

Temperature tolerance: Plants of the new *Angelonia* have been observed tolerate temperatures ranging from about 5° C. to 40° C.

It is claimed:

1. A new and distinct *Angelonia* plant named 'Zebra' as illustrated and described.

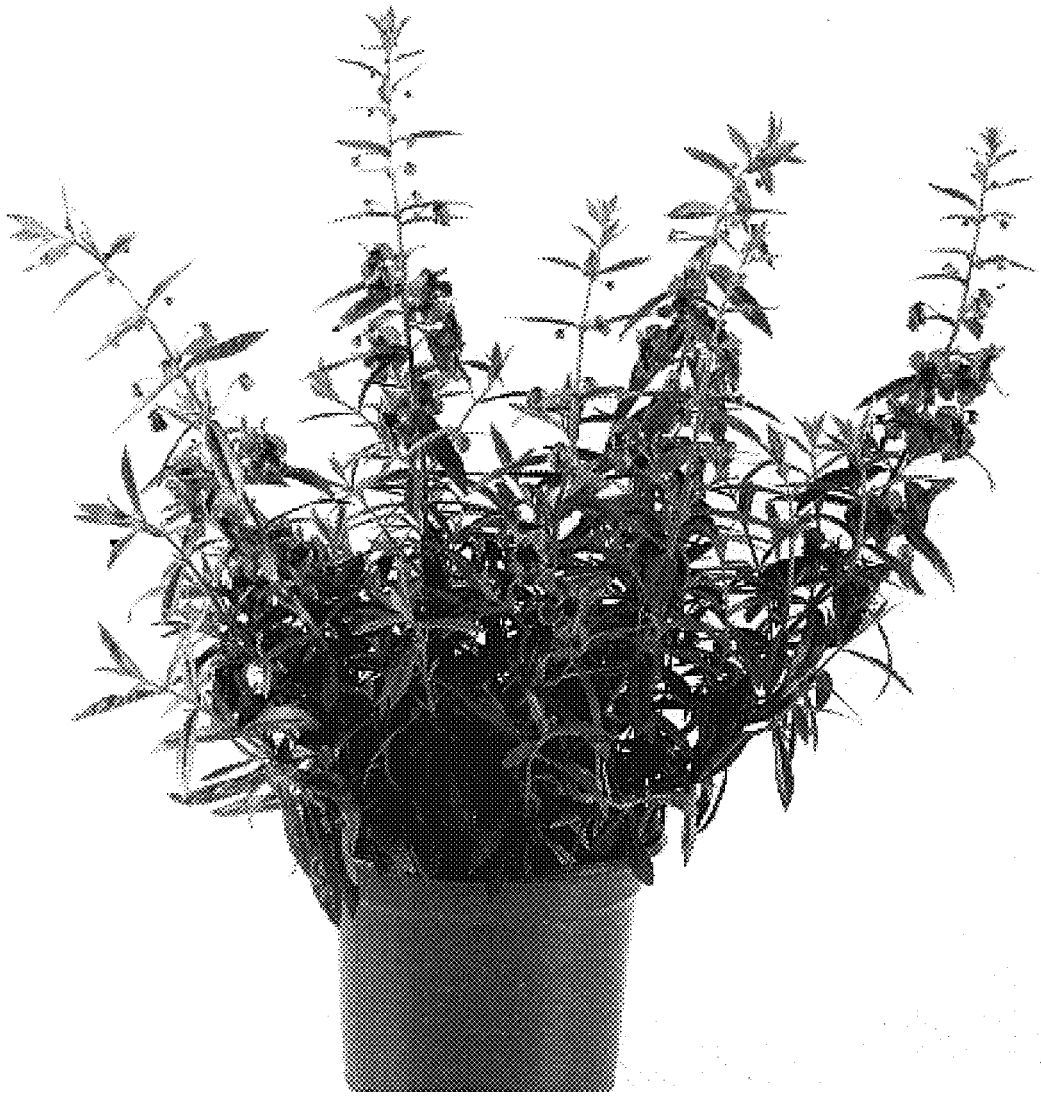

* * * * *